United States Patent [19]

Witholt et al.

[11] Patent Number: 5,334,698

[45] Date of Patent: Aug. 2, 1994

[54] PROCESS FOR PRODUCING POLYESTERS BY FERMENTATION: A PROCESS FOR PRODUCING OPTICALLY ACTIVE CARBOXYLIC ACIDS AND ESTERS: ARTICLES OF MANUFACTURE COMPRISING POLYESTER

[75] Inventors: Bernard Witholt, Eelde; Roland G. Lageveen, Groningen, both of Netherlands

[73] Assignee: Rijksuniversiteit te Groningen, Broerstraat, Netherlands

[21] Appl. No.: 770,180

[22] Filed: Oct. 2, 1991

Related U.S. Application Data

[62] Division of Ser. No. 127,216, Dec. 1, 1987, Pat. No. 5,135,859.

[30] Foreign Application Priority Data

Dec. 2, 1986 [NL] Netherlands ............... 8603073

[51] Int. Cl.⁵ ............... C08G 63/08; C08G 63/06; C12P 7/62
[52] U.S. Cl. ............... 528/354; 435/135; 435/136; 435/146; 435/280; 435/874; 528/361
[58] Field of Search ............... 528/354, 361; 435/135, 435/136, 146, 280, 874

[56] References Cited

U.S. PATENT DOCUMENTS

| | | | |
|---|---|---|---|
| 4,477,654 | 10/1984 | Holmes et al. | 528/361 |
| 5,023,316 | 6/1991 | Benvenuti et al. | 528/357 |

OTHER PUBLICATIONS

De Smet et al., Enzyme and Microbial Technology, vol. 5, 352–360 (1983).

*Primary Examiner*—John Kight, III
*Assistant Examiner*—Shelley A. Wright
*Attorney, Agent, or Firm*—Henry D. Coleman; R. Neil Sudol

[57] ABSTRACT

This invention relates to a process for producing polyester biopolymers by culturing *Pseudomonas oleovorans* bacteria on substrates comprising certain nutrients. The nature of the polyesters can be varied by varying the nature of the carbon source used. In this way polyesters with unsaturated double bonds can be produced, too. From the polyesters, optically active carboxylic acids or esters are produced. The polymers can be used for making articles of manufacture, such as sutures, films, skin and bone grafts.

6 Claims, 11 Drawing Sheets

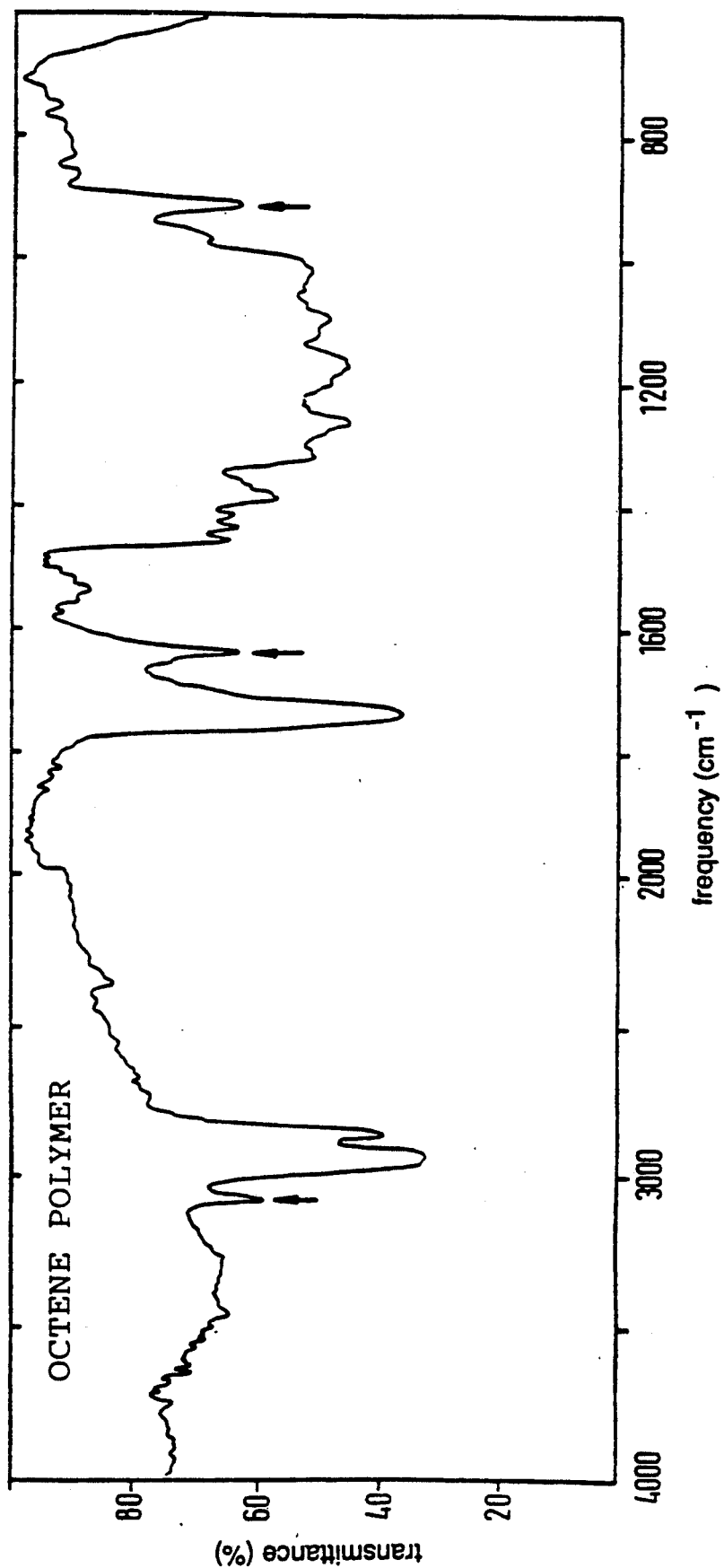

PROCESS FOR PRODUCING POLYESTERS BY FERMENTATION: A PROCESS FOR PRODUCING OPTICALLY ACTIVE CARBOXYLIC ACIDS AND ESTERS: ARTICLES OF MANUFACTURE COMPRISING POLYESTER

This is a division of application Ser. No. 07/127,216, filed on Dec. 1, 1987, now U.S. Pat. No. 5,135,859.

This invention relates to a process for producing polyesters by aerobic cultivation of micro-organisms with nutrient limitation.

A process of this type is disclosed in European patent publication 0015669. In it, there is described a preparation of poly(3-hydroxybutyric acid), designated by PHB, by aerobically culturing certain *Methylobacterium organophilum* strains with nutrient limitation, in particular nitrogen and/or phosphorus limitation. A possible source of carbon is the inexpensive methanol. Other micro-organisms have also been proposed for the production of PHB, e.g., Alcaligenes species, as described in European patent publication 0046344, and certain Pseudomonas strains, see Appl. Microbiol. Biotechnol. 23 (1986) 322-329.

PHB produced by microbiological means is a biodegradable, optically active polyester built up from units having the formula $-CO-CH_2-CH(CH_3)-O-$. This biopolymer has very interesting properties and can be put to many uses. The polymer can be moulded like other thermoplastics, can be reinforced with inorganic fillers, can be spun into fibers, and can be used for making films having excellent gas barrier properties. The biodegradable PHB can be converted with non-biodegradable polymers to form mixed polymers. Concrete uses are the use of PHB for making surgical yarn and artificial skin or artificial bone. Also, the optically active PHB can be converted into optically active monomers which, by chemical means, cannot be easily produced in optically pure form, and are suitable starting materials for organochemical conversions, e.g., for the synthesis of pharmaceutical products.

A disadvantage of PHB, however, is that it is not easy to vary the chemical structure of the polymer. This disadvantage can be avoided, according to U.S. Pat. No. 4,477,654, by carrying out the aerobic cultivation of Alcaligenes species at least in part in the presence of a carboxylic acid, such as propionic acid, or alkali metal salts or low alkyl esters thereof. The biopolymer thus formed is built up from 3-hydroxybutyrate residues having the structural formula $-CO-CH_2-CH(CH_3)-O-$, and less than 50 mole % residues of other hydroxy acids, such as residues having the structural formula $-CO-CH_2-CH(C_2H_5)-O-$. However, even with this known process, the possibilities of variation are very limited.

The research group to which the present inventors belong is investigating micro-organisms of the species *Pseudomonas oleovorans*. Various Pseudomonas species are able to grow on aliphatic or aromatic hydrocarbons as a source of carbon, whereby the assimilation begins with an oxygenation. This oxygenation is catalyzed by oxygenases, the genetic information for which is mostly associated with plasmids, such as the well-known OCT, CAM, TOL, XYL, SAL and NAH plasmids, which enable the first stages in the degradation of n-alkanes containing 6-12 carbon atoms; camphor; toluene and m- and p-xylene; salicylate; and naphthalene, respectively. *Pseudomonas oleovorans* strains containing an OCT plasmid coding for the monooxygenase ω-hydroxylase can grow on n-alkanes containing 6-12 carbon atoms because a terminal methyl group is converted into a hydroxymethyl group, whereafter further conversions via the aldehyde and the carboxylic acid lead to products fitting normal metabolism. They also have been found to be able to grow on different unsaturated hydrocarbons, such as 1-octene and 1,7-octadiene, with the first step often being the formation of a 1,2-epoxide.

As described by De Smet et al. in J. Bacteriol. 154 (1983) 870-878, it was observed during the cultivation of *Pseudomonas oleovorans* TF4-1L (ATCC 29347) in a nutrient medium containing 20 to 50% (vol/vol) n-octane that inclusions similar to the well-known poly-β-hydroxybutyrate inclusions of, for example, *Bacillus cereus* occurred in the cells. Further examination showed that these inclusions contain a polymeric material built up at least in part of β-hydroxy-octanoate units having the structural formula $-CO-CH_2-CH(C_5H_{11})-O-$.

It has now been found—and this constitutes the essence of the present invention—that a broad range of polyester type biopolymers can be produced by aerobically culturing *Pseudomonas oleovorans* bacteria, in which the chemical structure or composition of the biopolymer can be easily controlled by selecting the substrate. The invention renders it possible to produce polyester type biopolymers with side chains whose length can be varied in an adjustable manner, and which may contain a terminal double bound as to an adjustable portion.

The process according to the invention is characterized by culturing *Pseudomonas oleovorans* bacteria under aerobic conditions in a nutrient medium containing an excess of a carbon source and a limiting quantity of at least one of the other nutrients essential for growth, the carbon source comprising at least one assimilable acyclic aliphatic hydrocarbon compound, and if desired recovering the biopolymer formed from the cells.

A process according to the invention which leads to a biopolymer containing saturated side chains only is characterized by producing polyesters built up of units having the structural formula (1):

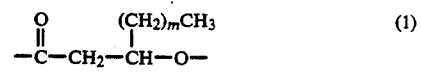

wherein m represents an integer of 2-8, by using a carbon source comprising one or more paraffins containing 6-12 carbon atoms or paraffin oxidation products. The term "paraffin oxidation products" as used herein means alkanols, alkanals, and alkanoic acids, which are produced as intermediates in the degradation of paraffin. These alternative substrates will especially be eligible when a *Pseudomonas oleovorans* strain is used without an OCT plasmid, at least without active paraffin hydroxylase. The number of carbon atoms of paraffin oxidation products may alternatively be outside the range of 6-12 carbon atoms, e.g., 4 or 14 carbon atoms, as the limitation of 6-12 carbon atoms for paraffins is related to the limitations of the paraffin-hydroxylase system.

The paraffins (or paraffin oxidation products) are preferably non-branched compounds, but it is not excluded that branched compounds can be used as well and built into the polymer.

A process according to the invention productive of a polymer containing both saturated and unsaturated side chains is characterized by producing polyesters built up of units having the structural formula (1):

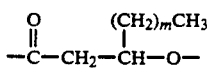

and units having the structural formula (2):

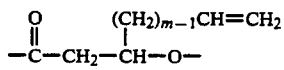

wherein m represents an integer of 2-8, by using a carbon source comprising one or more unbranched 1-alkylenes containing 6-12 carbon atoms and, if desired, also one or more non-branched paraffins or paraffin oxidation products containing 6-12 carbon atoms. Even when 1-alkylenes are used as the only carbon source, a portion of the side chains in the biopolymer formed is saturated. The ratio between saturated and unsaturated side chains, however, can be varied by the use of substrate mixtures, such as octane and octene.

This variant of the invention has the particular advantage that, owing to the terminal double bonds, the resulting biopolymer can easily be chemically modified in a controllable percentage of the side chains or crosslinked with other polymer chains.

A preferred embodiment of the invention is characterized by producing polyesters in which the side chains contain 3 carbon atoms (m=2), by using one or more substrates containing 6 carbon atoms. When a substrate is used which contains hexene or hexene+hexane, a portion of the side chains in the biopolymer will contain a terminal double bond.

Another preferred embodiment of the invention is characterized by preparing polyesters in which the side chains contain 4 carbon atoms (m=3) by using one or more substrates containing 7 carbon atoms. A polyester with terminal double bonds in a portion of the side chains is obtained when the substrate used is heptene or heptene +heptane.

Both of the above preferred embodiments are productive of polyesters in which, in essence, all side chains have the same number of carbon atoms. This is not the case with the preferred embodiments to be described hereinafter.

Such a preferred embodiment of the invention is characterized by producing copolymeric polyesters in which the side chains contain 3 and 4 carbon atoms (m=2 and 3) by using one or more substrates containing 6 carbon atoms and one or more substrates containing 7 carbon atoms. Within these, and all other embodiments, many variations are possible, both in the choice of the substrates and in the mutual ratios thereof, and these variations make it possible for the ratios of the various side chains in the biopolymer to be varied virtually ad infinitum. Thus, in this embodiment, combinations of hexane and heptane; hexene and heptene; hexane and heptane; hexene and heptane; hexane, hexene and heptane; hexane, hexene and heptene; hexane, heptane and heptene; hexene, heptane and heptane; and hexane, hexene, heptane and heptene can be used, and in each of these combinations the ratio between the several substrates can be selected as desired.

Another embodiment is characterized by producing copolymeric polyesters in which the side chains contain 3 and 5 carbon atoms (m=2 and 4) by using one or more substrates containing 8 carbon atoms, if desired in combination with one or more substrates containing 6 carbon atoms. The preferred substrate is 1-octene, if desired in combination with octane, hexane and/or hexene.

A next preferred embodiment is characterized by producing copolymeric polyesters in which the side chains contain 3, 4 and 5 carbon atoms (m=2, 3 and 4) by using one or more substrates containing 7 carbon atoms and one or more substrates containing 8 carbon atoms, if desired in combination with one or more substrates containing 6 carbon atoms.

A further preferred embodiment is characterized by producing copolymeric polyesters in which the side chains contain 4 and 6 carbon atoms (m=3 and 5) by using one or more substrates containing 9 carbon atoms, if desired in combination with one or more substrates containing 7 carbon atoms.

Still another preferred embodiment is characterized by producing copolymeric polyesters in which the side chains contain 3, 4, 5 and 6 carbon atoms (m=2, 3, 4 and 5) by using one or more substrates containing 8 carbon atoms and one or more substrates containing 9 carbon atoms, if desired in combination with one or more substrates containing 6 and/or 7 carbon atoms.

A next preferred embodiment is characterized by producing copolymeric polyesters in which the side chains contain 3, 5 and 7 carbon atoms (m=2, 4 and 6) by using one or more substrates containing 10 carbon atoms, if desired in combination with one or more substrates containing 6 and/or 8 carbon atoms.

A further preferred embodiment is characterized by producing copolymeric polyesters in which the side chains contain 3, 4, 5, 6 and 7 carbon atoms (m=2, 3, 4, 5 and 6) by using one or more substrates containing 9 carbon atoms and one or more substrates containing 10 carbon atoms, if desired in combination with one or more substrates containing 6, 7 and/or 8 carbon atoms.

Still another preferred embodiment is characterized by producing copolymeric polyesters in which the side chains contain 4, 6 and 8 carbon atoms (m=3, 5 and 7), by using one or more substrates containing 11 carbon atoms, if desired in combination with one or more substrates containing 7 and/or 9 carbon atoms. Yet another preferred embodiment is characterized by producing copolymeric polyesters in which the side chains contain 3, 4, 5, 6, 7 and 8 carbon atoms (m=2, 3, 4, 5, 6 and 7) by using one or more substrates containing 10 carbon atoms and one or more substrates containing 11 carbon atoms, if desired in combination with one or more substrates containing 6, 7, 8 and/or 9 carbon atoms.

A next preferred embodiment is characterized by producing copolymeric polyesters in which the side chains contain 3, 5, 7 and 9 carbon atoms (m=2, 4, 6 and 8) by using one or more substrates containing 12 carbon atoms, if desired in combination with one or more substrates containing 6, 8 and/or 10 carbon atoms. A further preferred embodiment is characterized by producing copolymeric polyesters in which the side chains contain 3, 4, 5, 6, 7, 8 and 9 carbon atoms (m=2, 3, 4, 5, 6, 7 and 8) by using one or more substrates containing 11 carbon atoms and one or more substrates containing 12 carbon atoms, if desired in combination with one or more substrates containing 6, 7, 8, 9 and/or 10 carbon atoms.

Preferably, according to the invention, one or more substrates containing 7-11 carbon atoms are used, most preferably one or more substrates containing 8-10 carbon atoms, as, in this way, the largest amounts of polymers are obtained in the cells.

The manner in which, and conditions under which, an aerobic culture of *Pseudomonas oleovorans* bacteria can be realized are known to those skilled in the art. Cultivation can be effected fed-batchwise or continuously. It is recommendable for the aerobic cultivation to be carried out at pH 5–9, preferably about 7, and at a temperature below 37° C., preferably about 30° C., and for the aerobic cultivation to be carried with adequate agitation at a dissolved oxygen tension preferably above 50% saturation with air.

The aerobic cultivation can, and preferably will be carried out in a system of two liquids, one of which is an aqueous phase containing the water-soluble nutrients and the bacteria, and the other of which is an apolar phase containing the substrate hydrocarbons.

As is also the case with the PHB producing microorganisms discussed before, the *Pseudomonas oleovorans* bacteria do not produce significant quantities of polymer until after there is a shortage of one of the nutrients essential for growth. Suitable nutrient limitations are, for example, nitrogen, phosphate, sulphur and magnesium limitations, but of these N limitation and P limitation are preferred in view of a higher polymer yield. Of these, N limitation is easier to realize and for that reason most preferred.

In practice, the procedure will commonly be such that the aerobic cultivation with nutrient limitation is preceded by an exponential growth phase without nutrient limitations until a cell density of at least 2 g/l is reached.

The stationary phase, in which inclusions are formed in the biopolymer, must not be continued too long, because, after reaching a maximum, the polymer concentration is again decreased. Preferably, therefore, the biopolymer containing cells formed in the stationary phase with nutrient limitation are harvested before a significant decrease in biopolymer content of the cells has taken place.

The biopolymer included in the cells need not necessarily be isolated, because the bacterial cells with the biopolymer inclusions therein can be directly used, as proposed, for example, in U.S. Pat. No. 3,107,172. For most uses, however, isolation and purification of the polymer will be desirable or necessary. For this purpose, many known per se methods can be used. The bacterial cells can be broken up in many ways which are well known to those skilled in the art, e.g., by using shear forces (by means of homogenizers, grinders, so-called "French press" and the like), by an osmotic shock treatment, by using sonorous or ultrasonorous vibrations, by enzymatic cell wall decomposition, or by spray drying the cell suspension. Subsequently the polymer can be separated from the other components in many known per se manners, including solvent extraction and centrifugation. One suitable method of isolation is described in the above article by De Smet et al., using isopycnic centrifugation. For isolation on a larger scale it is preferable for the biopolymer to be isolated by converting the harvested cells into spheroplasts, breaking these up by a treatment with sonorous vibrations, and separating, and if desired washing and drying, the top layer formed after centrifugation. Preferably, the conversion into spheroplasts is effected in the presence of sucrose. Centrifugation proceeds satisfactorily if the mass is centrifuged for about 30 minutes at 10,000 g. The polymer then forms a white top layer on the supernatant and can easily be separated. Contaminations can be removed by washing, whereafter the washed polymer is brought into a suitable dry form preferably by freeze drying.

Another, highly suitable isolation procedure is as follows. Cells are harvested by means of a continuous centrifuge and then freeze dried. The dry cells are resuspended in, e.g., chloroform and subsequently extracted under reflux conditions for, for example, 4 hours. After cooling, the suspension is filtered and evaporated, for example, to a volume of 50 to 100 ml. The resulting polymer solution then contains, in addition to the polyester, a large amount of lipids and fatty acids. These are removed by precipitating the polymer in, for example, a 10-fold excess of ethanol. After settling of the polymer, the supernatant is decanted and the polymeric precipitate is dried by passing compressed air over it. The polymer is then preferably dissolved in as little chloroform as possible and subsequently, after filtration, re-precipitated in a 10-fold excess of ethanol. The resulting precipitate is then again dissolved in a minimum volume of chloroform, whereafter the synthetic plastics material can be obtained by pouring the solution into a mould and evaporating it. Evaporation can be accelerated by incubating the material under vacuum at 50° C. for some time.

The uses mentioned for PHB hereinbefore also apply to the polyester produced in accordance with the present invention. Particularly notable is the possibility of chemically modifying the resulting biopolymers, which possibility can in particular be well carried out when the polyester contains side chains with terminal double bonds. Cross-linking with other polymer chains, too, is possible.

The invention also provides a process for producing optically active carboxylic acids or esters, which is characterized by hydrolyzing a polyester produced in accordance with the invention, and if desired esterifying the resulting monomers. As stated before, such optically active compounds cannot be easily obtained in an optically pure form by chemical means. The invention accordingly provides an easily performed process for producing such optically pure compounds, which may have utility as intermediates in the production of, for example, pharmaceutical products, or purely scientific and/or application-directed research. If, as a result of the substrate used, the process produces different monomers, these can, if desired, be separated in a known per se manner, using the differences in chain length and/or saturation of the monomers.

The invention is illustrated in and by the following experimental section.

Part A shows the GLC pattern of the cells cultivated on octane after the assay. The peaks indicated by arrows are from the polymeric material. The peak at t=5 min represents the internal standard (benzoic acid methylester).

Part B shows the MS pattern of the most important GLC peak. The peak at 175 is the protonated form of the 3-hydroxyoctanoate methyl ester monomer, the peak at 192 represents NH4-3-hydroxyoctanoate methyl ester.

Part C shows the MS pattern of the smaller GLC peak. The peaks at 147 and 164 respectively represent the protonated and the ammonium derivative of 3-hydroxyhexanoate methyl ester.

Figure 3:
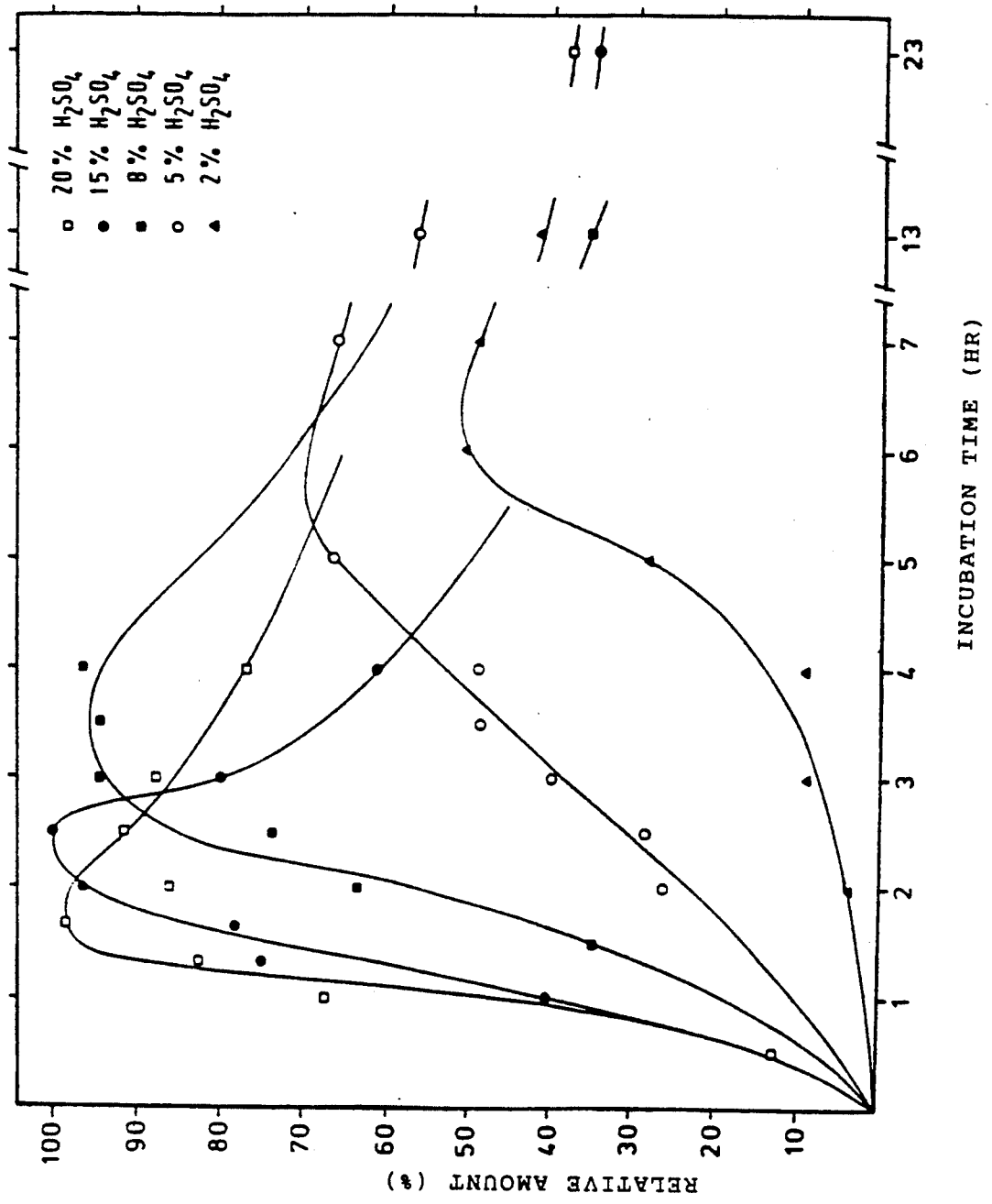

FIG. 3 concerns an assay for determining the amount of biopolymer in samples of a *Pseudomonas oleovorans* culture and shows a graph in which the effect of the incubation time and the sulphuric acid concentration in the hydrolysis and methanolysis of the biopolymer, produced on octane, on the amount of biopolymer is shown. For the measurements, identical cell pellets were used.

Figure 4:
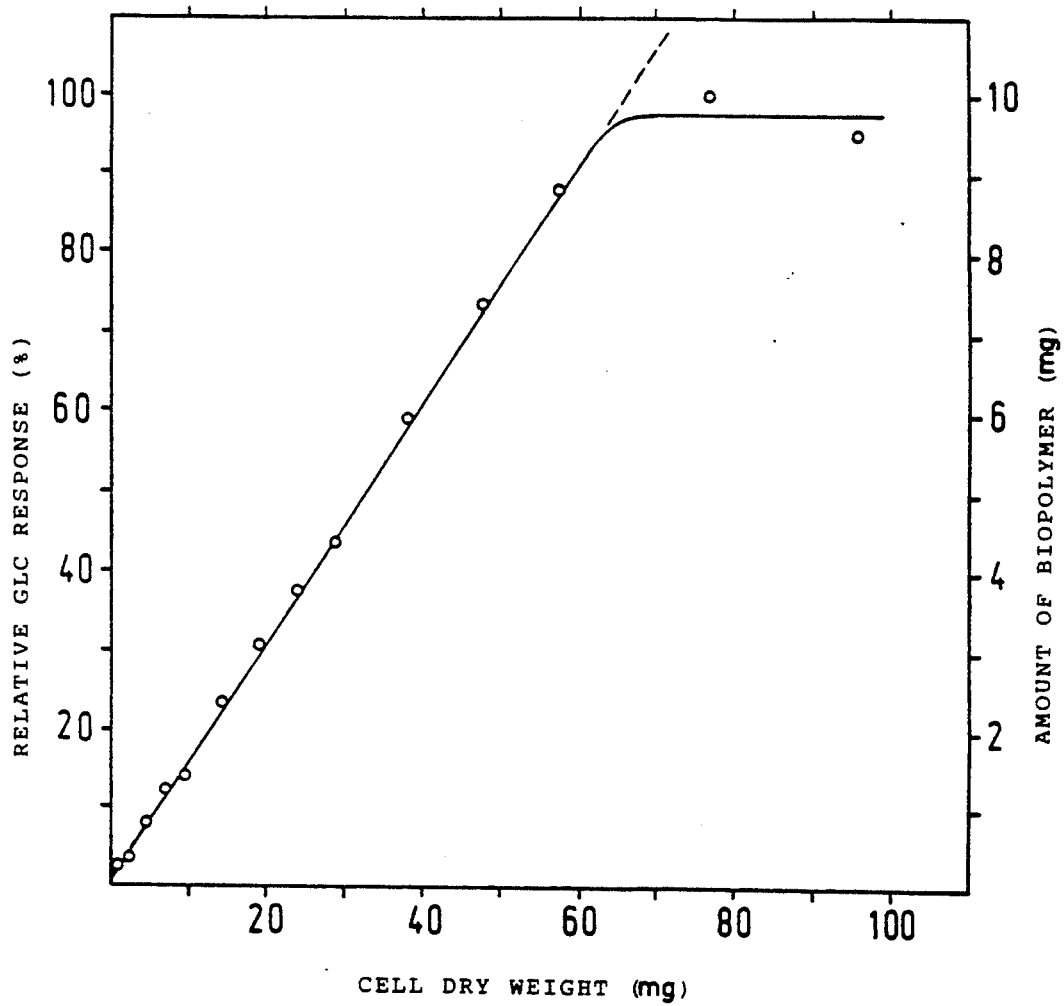

FIG. 4 shows the linearity of the poly-3-hydroxyalkanoate assay. The relative GLC response has been plotted against the amount of cell mass used in the assay.

FIGS. 5A-D shows the biopolymer production on n-octane in relation to the nutrient limitation used in the medium. Graph A relates to the case of nitrogen limitation, graph B the case of magnesium limitation, graph C the case of phosphate limitation, and graph D the case of sulphur limitation. The black (solid) signs indicate cell density, and the white (open) signs the amount of biopolymer.

FIGS. 6A-F shows the production of poly-3-hydroxyalkanoates by *P. oleovorans* after growth on various n-paraffins during nitrogen limitation. The paraffins used are n-hexane (graph A), n-heptane (graph B), n-nonane (graph C), n-decane (graph D), n-undecane (graph E) and n-dodecane (graph F). The solid signs indicate cell density, and the open signs the amount of biopolymer.

Figure 7:
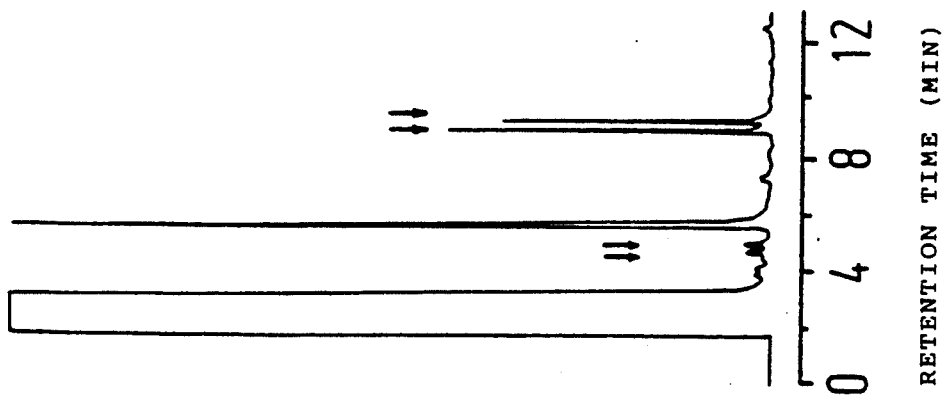

FIG. 7 shows the result of GLC analysis of the biopolymer formed by *P. oleovorans* after growth on 1-octene. The first cluster of peaks indicates the presence of 3-hydroxyhexenoate and 3-hydroxyhexanoate. The second pair of peaks indicates the presence of 3-hydroxyoctenoate and 3-hydroxyoctanoate. The unsaturated compounds have in each case the shorter retention time as determined by GLC/MS analysis. The relevant peaks are designated by arrows.

Figure 8A:
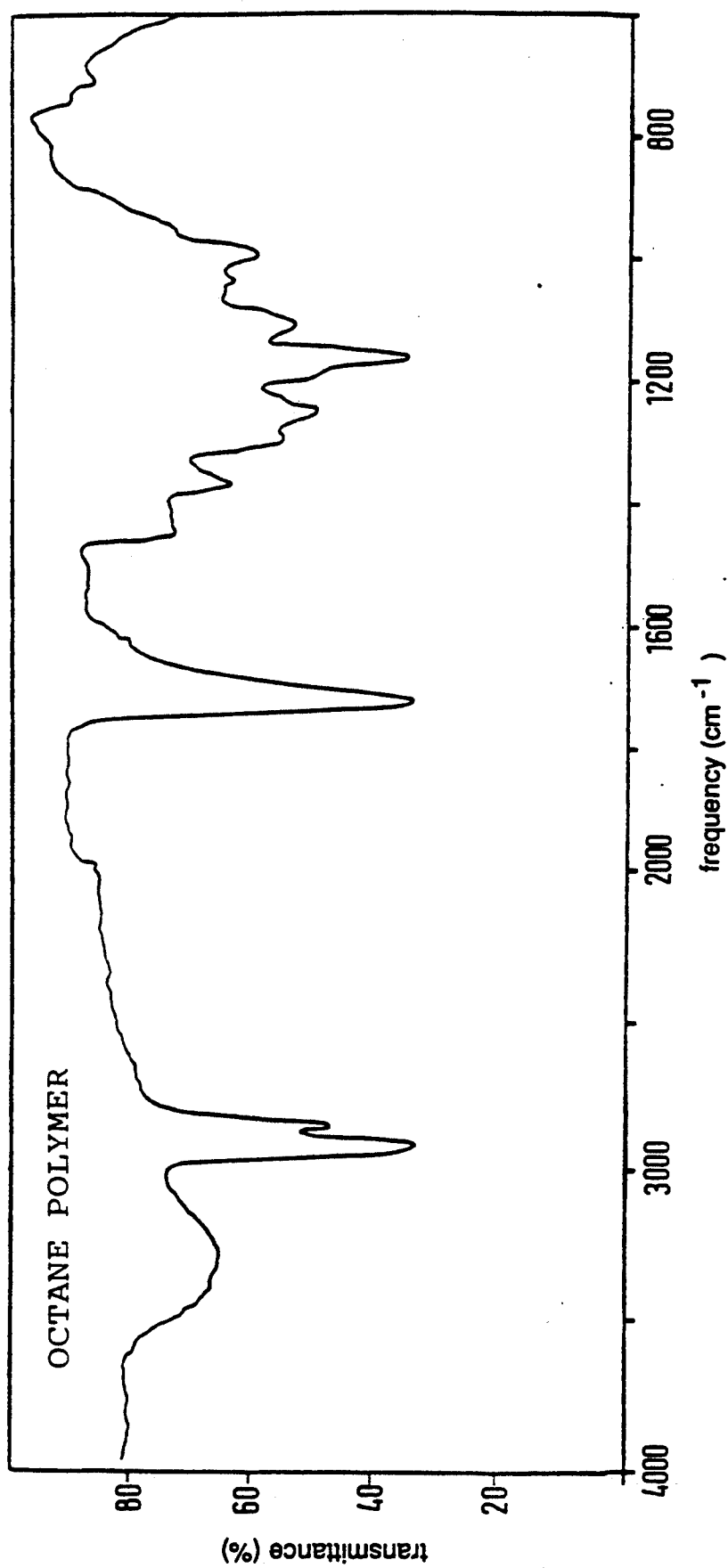

FIGS. 8A-B shows the infrared spectra of the biopolymers formed on octane (part A) and octene (part B). The arrows in part B indicate the absorptions caused by the terminal double bond in about 50% of the monomers.

1. Structure of the Biopolymers

The biosynthesis of a polymeric material by *Pseudomonas oleovorans* during growth on octane was described for the first time by De Smet et al. in 1983. The polymer was identified by means of elemental analysis, infrared spectroscopy and gas chromatography of the methanolyzed monomers as a poly-3-hydroxybutyrate-like (PHA) polyester, probably poly-3-hydroxyoctanoate. After that, three identification compounds have been synthesized by organochemical routes (Ketelaar et al., Tetrahedron Letters 26 (1985), 4665-4668), whereafter it was possible to determine the absolute structure of the polymer.

Figure 1:
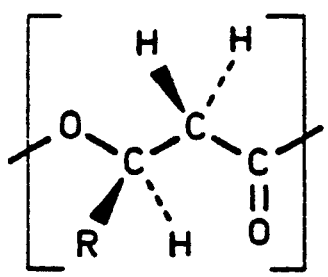
FIG. 1 shows the generic structural formula of the structural units of the biopolymer produced by the process according to the invention. In it, R represents an alkyl group —$(CH_2)_m CH_3$ or an alkenyl group —$(CH_2)_{m-1}$—CH=$CH_2$, in which m represents an integer of 2–8. In case octane is used as the substrate, the biopolymer is a copolymer of the monomers (R)-3-hydroxyhexanoate (R=$C_3H_7$) and (R)-3-hydroxyoctanoate (R=$C_5G_{11}$).

After comparing the methanolyzed monomers with the synthesized (S)-3-hydroxyhexanoate methyl ester, (S)-3-hydroxyoctanoate methyl ester and (S)-3-hydroxydecanoate methyl ester, it has been established that the polymer formed by *P. oleovorans* after growth on octane consists of (R)-3-hydroxyhexanoate and (R)-3-hydroxyoctanoate. The general structural formula of the polymer formed after growth on octane is given in FIG. 1.

Identification of monomers of other polymers formed (see below) was effected by acid methanolysis of the polymer, whereafter the monomeric methyl esters formed were analyzed by means of gas chromatography coupled mass spectrometry.

2. Assay

In order to analyze the kinetics of the formation of the intracellularly stored polymer, we have developed a reproducible method, by means of which the instantaneous amount of polymer can be determined in small culture samples (biomass). This method has been developed based on the method of Braunegg et al. (Eur. J. Microbiol. Biotechnol. 6 (1978) 29-37) for the determination of poly-3-hydroxybutyrate in microbial biomass.

Figure 2B:
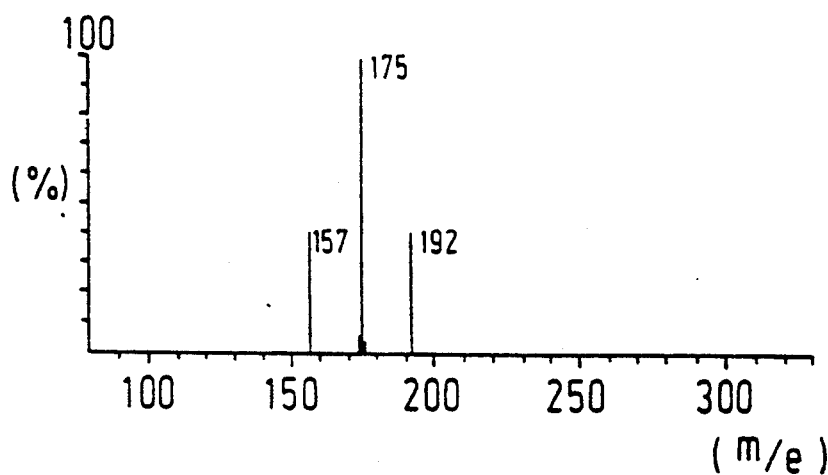
FIGS. 2A-C shows the results of gas chromatographic (GLC) and mass spectrum (MS) analysis of the biopolymer produced on octane.
Figure 2C:
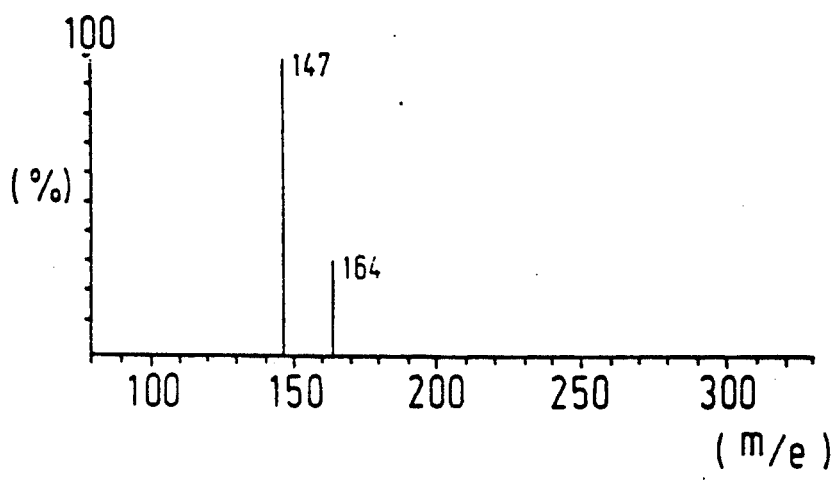
Figure 2A:
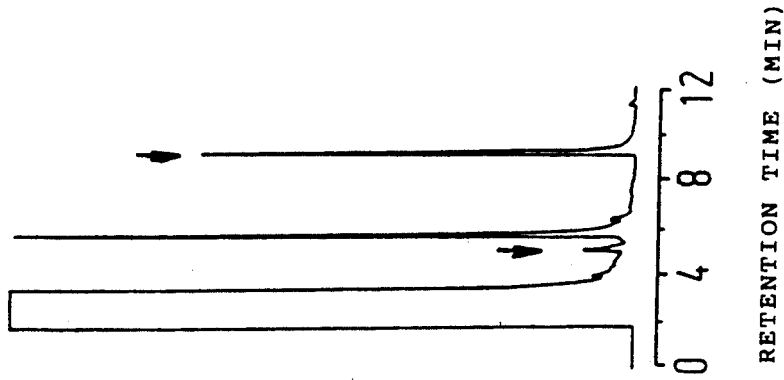

According to that method, whole samples of the cell culture are simultaneously hydrolyzed and methanolyzed, whereafter the monomeric methyl esters formed from the polymer are analyzed by means of gas chromatography. A typical gas chromatogram with mass spectra of the two peaks is shown in FIG. 2.

To develop this method for the Pseudomonas polymer, identical cell samples of a stationary phase culture of *P. oleovorans* on n-octane were hydrolyzed at 100° C. at various times and at different concentrations of sulphuric acid in methanol (FIG. 3). After further optimizations with regard to the extraction period and the introduction of a drying procedure of the GLC samples, the assay was programmed as follows:

Cell samples with a volume of 0.1 to 4.0 ml are centrifuged in an Eppendorf centrifuge for 3 minutes, whereafter the supernatant is removed and the pellet is freeze dried. The freeze dried pellet is subsequently resuspended in 2 ml 15% (v/v) sulphuric acid in methanol, to which 2 ml chloroform is added. In a test tube with screw cap, these samples are incubated at 100° C. for 140 minutes with stirring using a magnetic stirrer. After cooling the samples on ice, 1.0 ml water is added and the monomeric methyl esters are extracted by vortexing the contents of the tube for 20 seconds. After phase separation, accelerated by centrifugation (5 min., 4000×g), the aqueous layer is removed and the organic phase is dried on anhydrous $Na_2SO_4$. The samples are subsequently gas chromatographed using benzoic acid methyl ester as the internal standard.

The linearity of the assay is illustrated by FIG. 4. The assay is linear up to 9 mg biopolymer per sample.

3. Formation of Biopolymer During Growth and Nitrogen Limitation

For all experiments, except those specified under point 9, use was made of *Pseudomonas oleovorans* TF4-1L (ATCC 29347).

For fermentations, *P. oleovorans* was pre-cultured overnight on 50 ml E-medium with 2% octane in 250 ml Erlenmeyer flasks at 30° C. on a shaking plate (200 rpm) for 16 hours. E-medium has the following composition:

| | |
|---|---|
| MgSO$_4$.7H$_2$O | 0.2 g/l |
| trisodium citrate | 2.0 g/l |
| NaNH$_4$.HPO$_4$.4H$_2$O | 3.5 g/l |
| K$_2$HPO$_4$ | 10.0 g/l |
| 1000 * MT | 1 ml/l |

1000 * MT is a solution of spore elements in 1N HCl and is added after sterilization of the other components. 1000 * MT has the following composition:

| | |
|---|---|
| FeSO$_4$.7H$_2$O | 2.78 g/l |
| MnCl$_2$.4H$_2$O | 1.98 g/l |
| CoSO$_4$.7H$_2$O | 2.81 g/l |
| CaCl$_2$.2H$_2$O | 1.47 g/l |
| CuCl$_2$.2H$_2$O | 0.17 g/l |
| ZnSO$_4$.7H$_2$O | 0.29 g/l | dissolved in 1N HCl.

Main cultures were carried out in 500 ml E*-medium in 1 l fermentors (continuous stirred tank reactors, CSTR), with the pH being maintained at 6.9, which is the optimum value for growth, by computer-controlled addition of 5% NH$_3$ and 1N H$_2$SO$_4$. During the fermentations, an oxygen tension (dissolved oxygen tension D.O.T.) of 60% air saturation was maintained by means of a computer-controlled valve in the air inlet tube. The medium was stirred at a rate of 600 rpm.

E*-medium has the following composition:

| | |
|---|---|
| K$_2$HPO$_4$.3H$_2$O | 7.5 g/l |
| NaNH$_4$HPO$_4$.4H$_2$O | 3.5 g/l |
| KH$_2$PO$_4$ | 3.7 g/l |
| 1000 * MT | 1 ml/l |
| 100 mM MgSO$_4$ | 10 ml/l |

1000 * MT and the sterile MgSO$_4$ solution were only added after sterilization of the other components. As the only carbon and energy source, 10–20% (v/v) of octane was added. Using this medium in combination with pH titration by means of ammonia, it was possible to obtain a cell density of 6.5 mg/ml.

Throughout the entire fermentation, the cell density (Witholt, J. Bacteriol. 109 (1972) 350–364) and the amount of polymer formed (according to point 2) was monitored by taking samples.

Figure 5A:
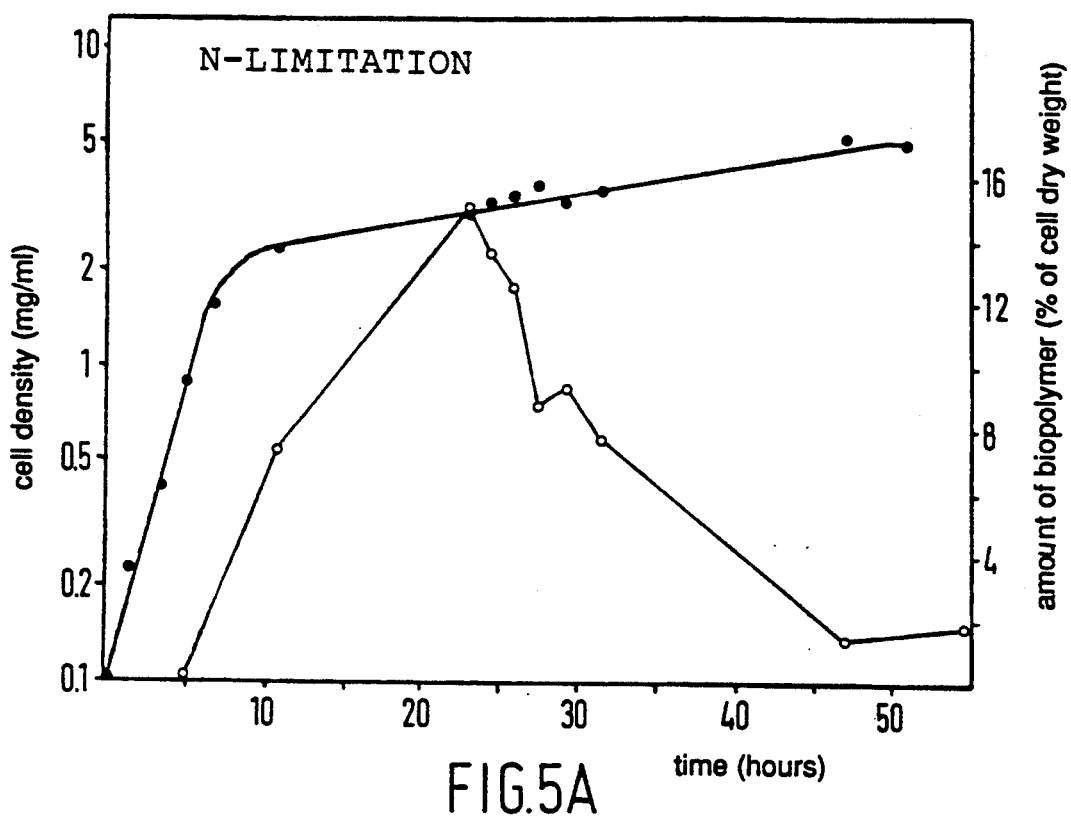
Figure 5B:
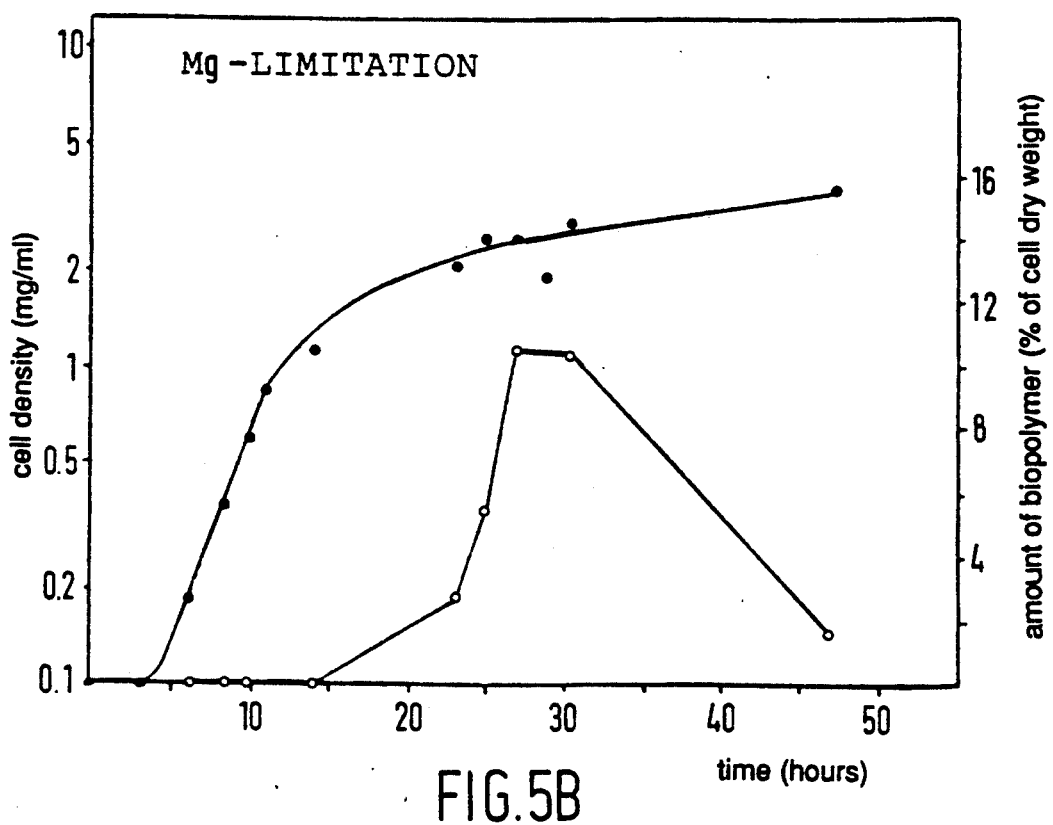
Figure 5C:
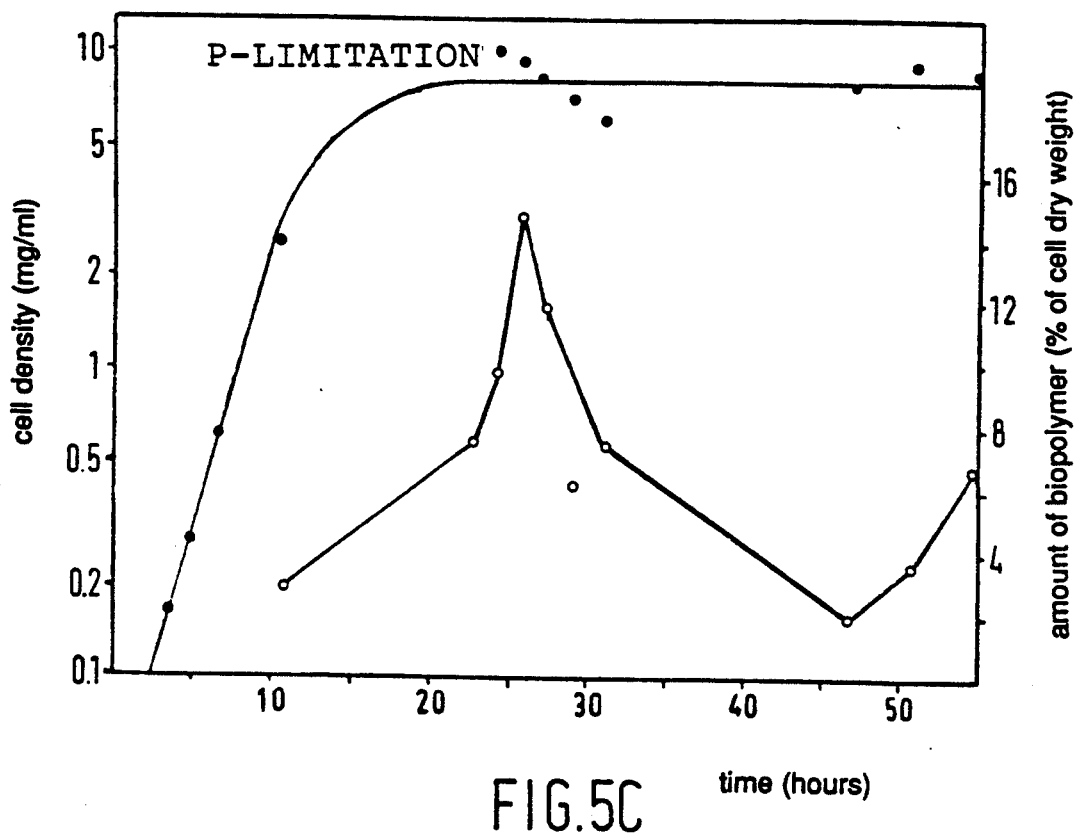
Figure 5D:
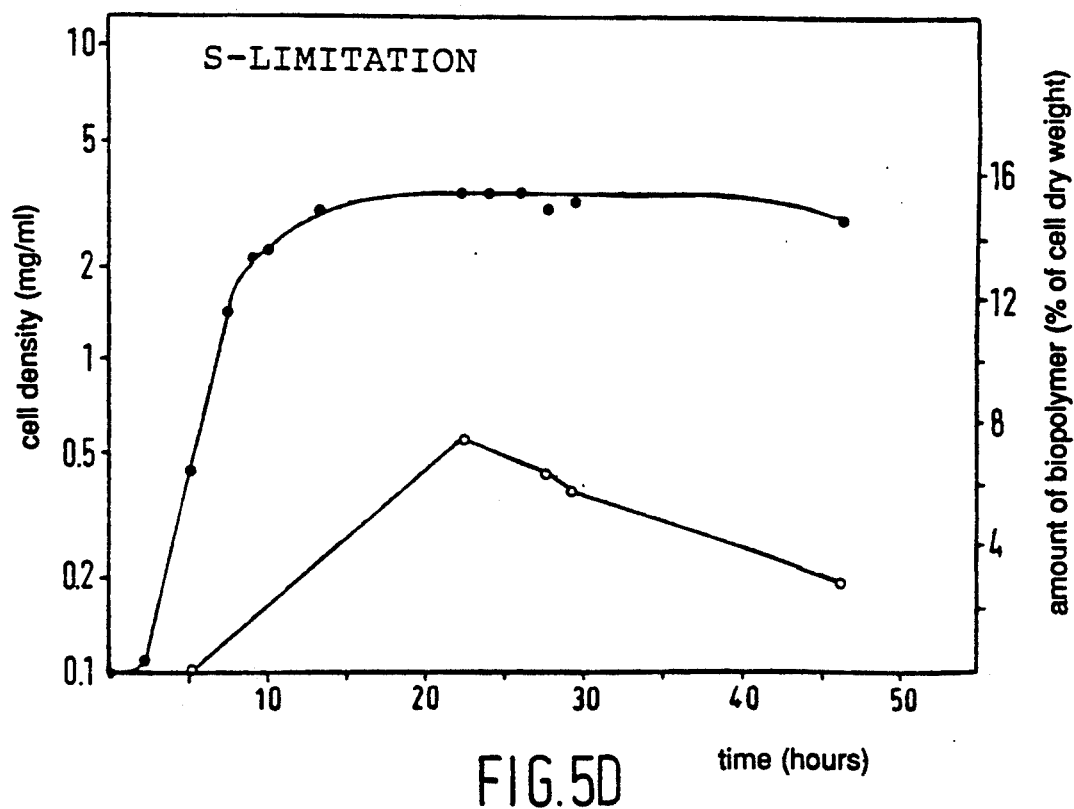
Figure 6A:
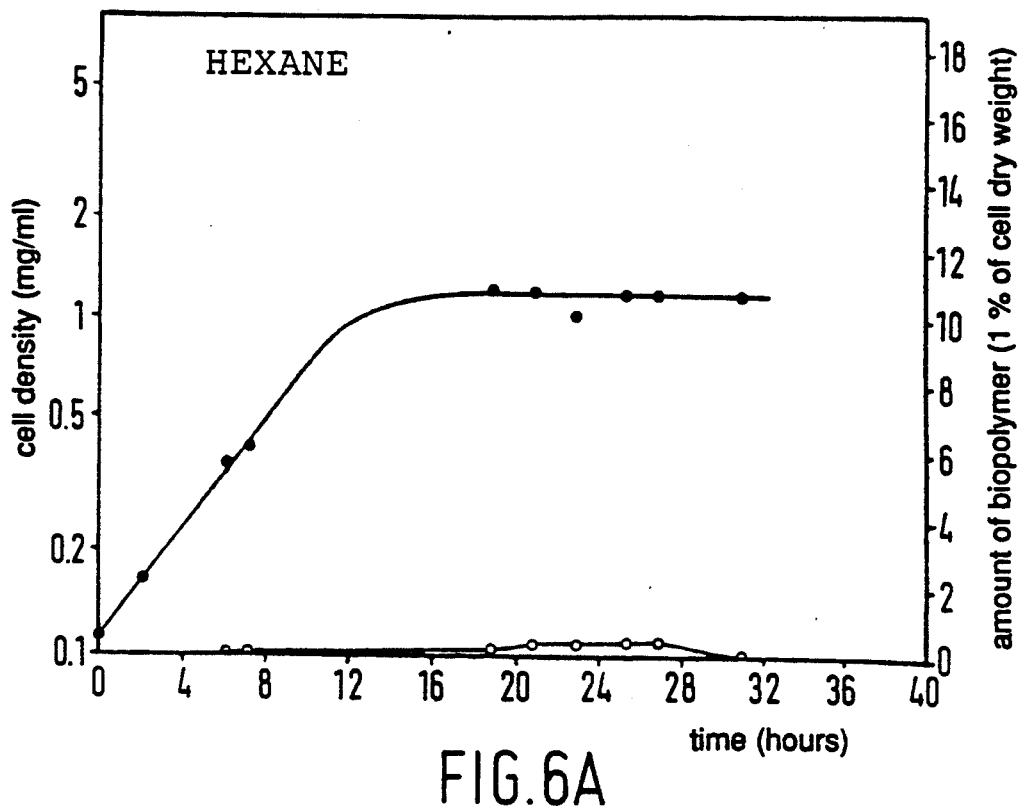
Figure 6B:
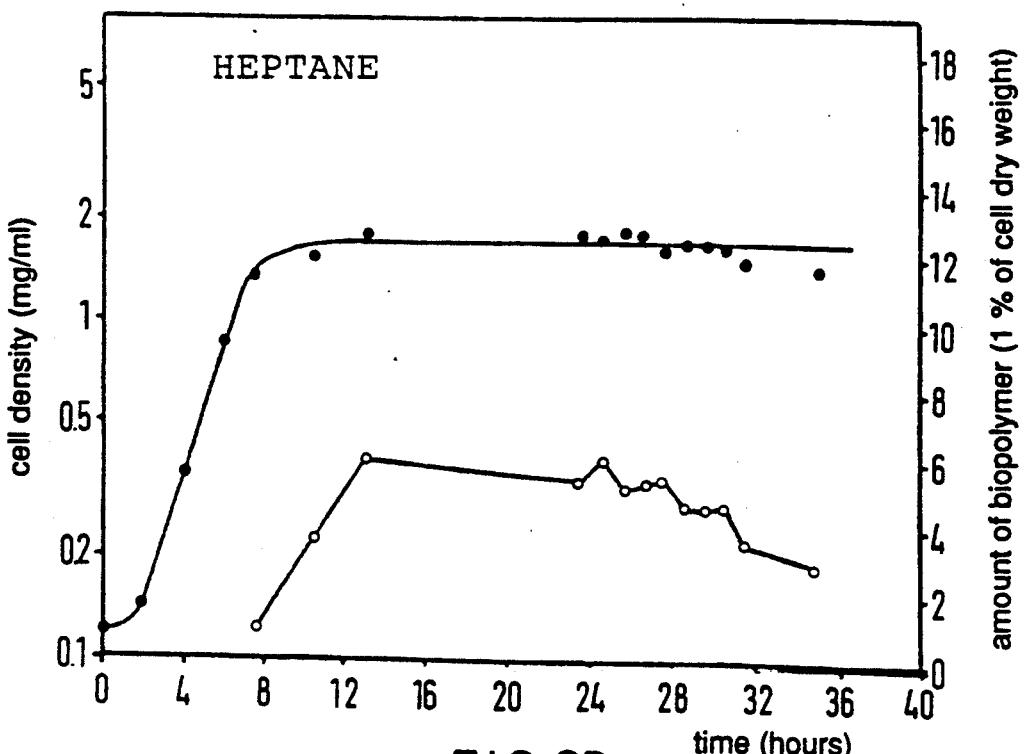
Figure 6C:
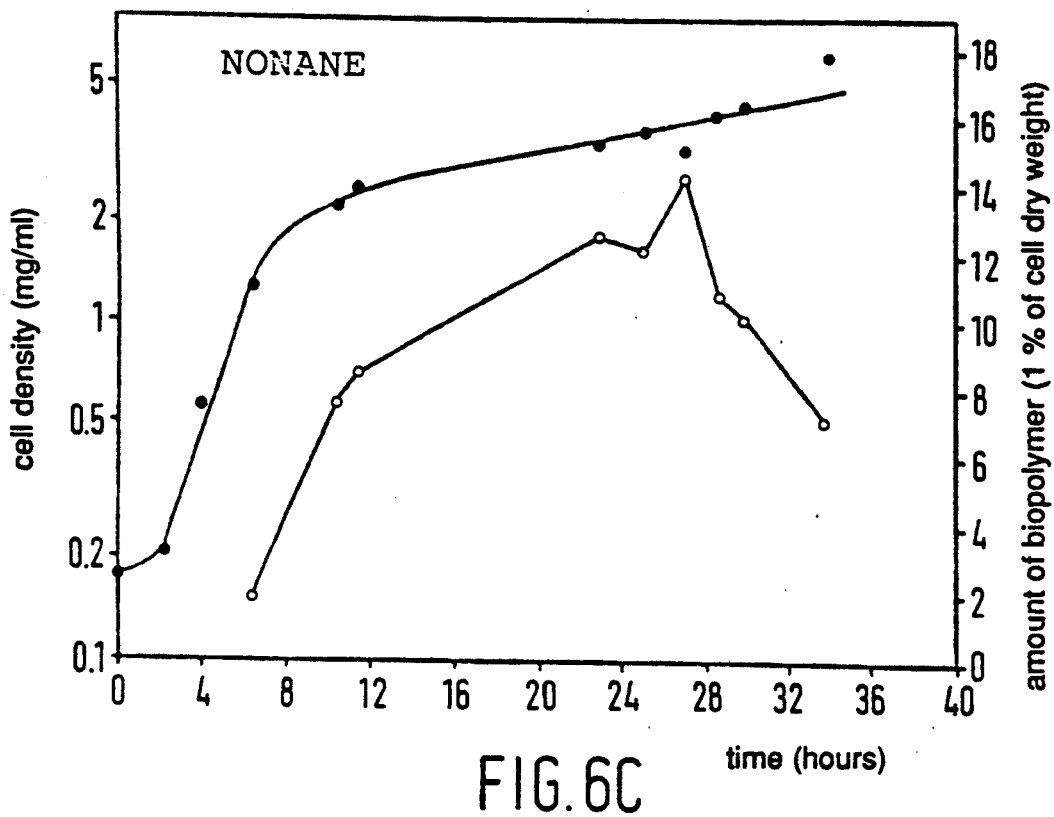
Figure 6D:
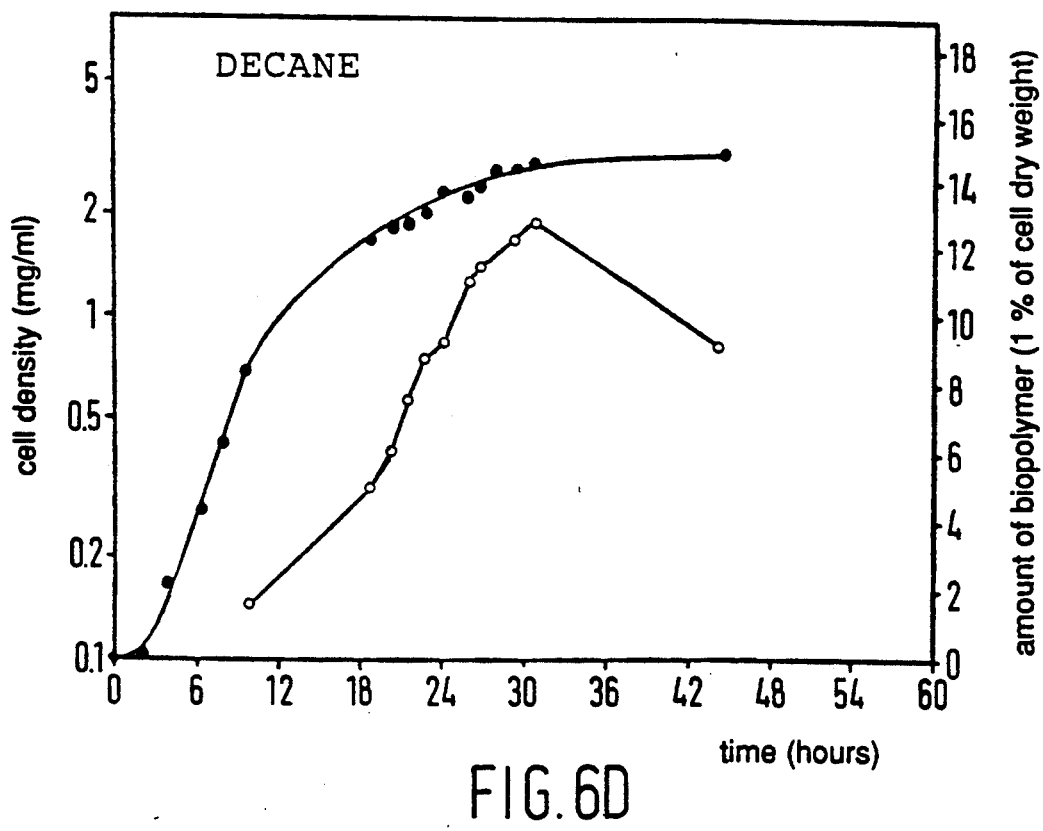
Figure 6E:
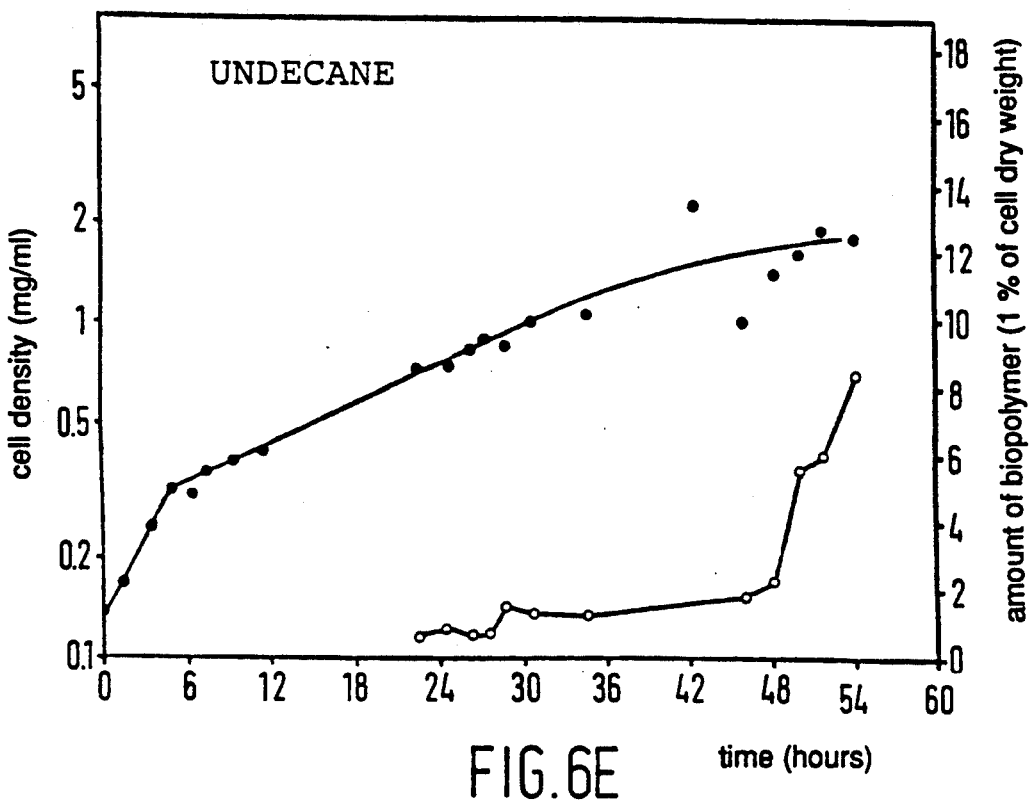
Figure 6F:
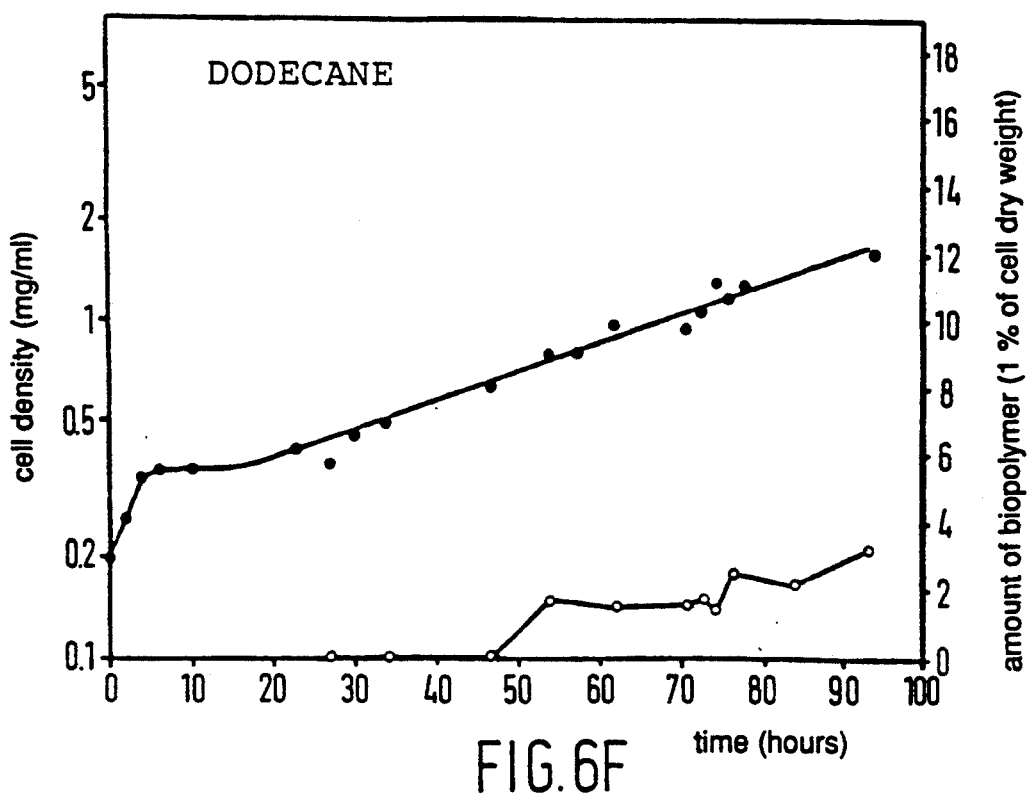

FIG. 5A shows that during the exponential growth phase ($\mu_{max}=0.48$) there is virtually no production of biopolymer. However, when the rate of growth decreases as a result of limitation of one of the nutrients (in this case nitrogen), polymer formation starts (maximum 15% of the cell dry weight).

The nitrogen limitation referred to was effected as follows:

N limitation: E*-medium was used with the pH of the culture being controlled by adding 2N KOH and 1N H$_2$SO$_4$. In this way, a cell density of 2 mg per ml can be achieved.

4. Biopolymer Formation with Other Limitations

P. oleovorans was pre-cultured as specified under point 3. For the main cultures, depending on the nutrient on which limitation was effected, an adapted E*-medium was used:

P limitation: E*-medium, diluted 40 times and supplemented with nitrogen in the form of NH$_4$Cl up to 17 mM, was used. The pH of the culture was kept constant with 2N KOH and 2N H$_2$SO$_4$. The phosphate present in this medium enables cell growth up to 2 mg/ml.

S limitation: To E*-medium, instead of 100 mM MgSO$_4$, an amount of MgSO$_4$ was added up to a final concentration of 0.4 mM and an amount of MgCl$_2$ was added up to a final concentration of 0.6 mM. The pH was controlled using 5% ammonia. On this medium a cell density of 2 mg/ml is possible.

Mg limitation: To E*-medium, instead of 100 mM MgSO$_4$, an amount of MgSO$_4$ was added up to a final concentration of 0.1 mM and an amount of Na$_2$SO$_4$ was added up to a final concentration of 0.9 mM. The pH was controlled using 5% ammonia. On this medium, a cell density of 1 mg/ml can be achieved.

During the entire fermentation, the cell density of the culture and the amount of polymer formed was measured as indicated under point 3 above.

Using these media, it is again seen that the production of polymer takes place mainly in the stationary phase. Depending on the limitation, the percentage of biopolymer of the cellular dry weight varies as shown in FIG. 5. The following Table 1 shows the effect of these nutrient limitations on the amount of polymer formed, indicated as percent of cellular dry weight:

TABLE 1

| effect of limitations on polymer formation. | |
|---|---|
| limitation | polymer (%) |
| P | 15 |
| S | 7 |
| Mg | 10 |
| N | 15 |

In general, it can be concluded that the formation of polymer is best under nitrogen and phosphate limitation.

5. Formation of Polymer on Other Paraffins

Using the optimum conditions under which poly-3-hydroxy-alkanoates are formed, determined as described under point 4 above, other paraffins were tested as a possible substrate for polymer formation. As the literature shows that P. oleovorans can grow on C$_6$ to C$_{12}$ n-paraffins, these compounds were tested first.

Pre-cultures were conducted as described under point 3 above, and main cultures as described under point 4 above under N-limiting conditions. Cell densities and polymer percentages were determined as indicated under point 3 above.

The results of growth and polymer formation are summarized in FIG. 6. Table 2 shows the amount of polymer maximally formed, the time after which this maximum occurs, and the monomeric composition of the polymers formed.

TABLE 2

| Biopolymers and their composition formed by Pseudomonas oleovorans on different n-alkanes | | | | | | | | | |
|---|---|---|---|---|---|---|---|---|---|
| carbon source | amount of polymer (1) | fermentation time (hrs) (2) | polymer composition (3) | | | | | | |
| | | | 3-OH-C6 | 3-OH-C7 | 3-OH-C8 | 3-OH-C9 | 3-OH-C10 | 3-OH-C11 | 3-OH-C12 |
| hexane | 1.2 | 22 | 1 | | | | | | |

TABLE 2-continued

Biopolymers and their composition formed by *Pseudomonas oleovorans* on different n-alkanes

| carbon source | amount of polymer (1) | fermentation time (hrs) (2) | 3-OH-C6 | 3-OH-C7 | 3-OH-C8 | 3-OH-C9 | 3-OH-C10 | 3-OH-C11 | 3-OH-C12 |
|---|---|---|---|---|---|---|---|---|---|
| heptane | 6.7 | 22 |  | 1 |  |  |  |  |  |
| octane | 12.5 | 31 | 0.11 |  | 0.89 |  |  |  |  |
| nonane | 9.2 | 27 |  | 0.33 |  | 0.67 |  |  |  |
| decane | 12.5 | 31 | 0.10 |  | 0.66 |  | 0.24 |  |  |
| undecane | 8.4 | 54 |  | 0.23 |  | 0.63 |  | 0.14 |  |
| dodecane | 3.4 | 54 | 0.02 |  | 0.31 |  | 0.36 |  | 0.31 |

(1) maximal amount of biopolymer in g/g cell dry weight
(2) fermentation time at which the maximal amount of biopolymer is reached, in hours
(3) relative composition of the biopolymer in the different monomers:
3-OH-C6: 3-hydroxy-hexanoate
3-OH-C7: 3-hydroxy-heptanoate
3-OH-C8: 3-hydroxy-octanoate
3-OH-C9: 3-hydroxy-nonanoate
3-OH-C10: 3-hydroxy-decanoate
3-OH-C11: 3-hydroxy-undecanoate
3-OH-C12: 3-hydroxy-dodecanoate It is seen that *P. oleovorans* is capable of forming polymer on all these paraffins. The substrates known to be the best growth substrate, octane and nonane, are also the best substrate for polymer formation. The composition of the polymer depends on the substrate offered. After growth on C-even paraffins, C-even monomers are built-in in all instances, and on C-odd paraffins always C-odd monomers. The monomers are always 3-hydroxy-alkanoates, varying in chain length from substrate length to $C_6$. For $C_8$ and $C_9$ monomers, the polymer forming enzyme appears to have the highest specificity.

6. Formation of Biopolymer on Olefins

As *P. oleovorans* can also utilize n-olefins as the only source of carbon and energy, it has been investigated whether biopolymers can also be formed on these substrates. The fermentations to study this have been carried out as described under point 5 above. Cell densities and polymer percentages were determined as indicated under 3.

The polymer produced after growth on these unsaturated paraffins turns out to have a different composition from the paraffinic polymer, in that a portion of the monomers contains a terminal double bond.

In the case of polymer formed on n-octene, the amount of monomers with such a double bond is found to be 55% of the total. A typical GC spectrum of the hydrolyzed polymer formed on octene is shown in FIG. 7. IR spectra of the polymer formed on octane and octene are shown in FIG. 8. The peaks from the double bond (indicated by arrows) are clearly seen.

Table 3 shows the amount of polymer maximally formed after growth on the various olefins, the time required to reach this maximum, and the monomers the polymers consist of.

TABLE 3

Production of biopolymers by *Pseudomonas oleovorans* during growth on n-alkenes

| carbon source | amount of polymer (%) | fermentation time (hrs) | monomers (1) |
|---|---|---|---|
| n-octene | 8.0 | 25.0 | 3-OH-6:0; 3-OH-6:1; 3-OH-8:0; 3-OH-8:1 |
| n-nonene | 6.3 | 24.0 | 3-OH-9:0; 3-OH-9:1 |
| n-decene | 3.4 | 26.0 | 3-OH-8:0; 3-OH-8:1; 3-OH-10:0; 3-OH-10:1 |

(1): Composition of the biopolymers in the different monomers:
3-OH-6:0: 3-hydroxyhexanoate
3-OH-6:1: 3-hydroxy-5-hexenoate
3-OH-7:0: 3-hydroxyheptanoate
3-OH-7:1: 3-hydroxy-6-heptenoate
3-OH-8:0: 3-hydroxyoctanoate
3-OH-8:1: 3-hydroxy-7-octenoate
3-OH-9:0: 3-hydroxynonanoate
3-OH-9:1: 3-hydroxy-8-nonenoate
3-OH-10:0: 3-hydroxydecanoate
3-OH-10:1: 3-hydroxy-9-decenoate
3-OH-11:0: 3-hydroxyundecanoate
3-OH-11:1: 3-hydroxy-10-undecenoate
3-OH-12:0: 3-hydroxydodecanoate
3-OH-12:1: 3-hydroxy-11-dodecenoate

*P. oleovorans* is seen to be able to form biopolymers on 1-octene, 1-nonene and 1-decene. No polymer formation has as yet been detected after growth on hexene. The way in which the polymers are composed from their monomers is similar to that of the polymers formed on n-paraffins. It is striking, however, that the biopolymer formed during growth on 1-decene does not contain any detected quantities of $C_6$ monomers.

Based on the results obtained with the 1-olefins tested, biopolymer formation can also be expected to take place on 1-heptene, 1-undecene and 1-dodecene.

7. Formation of Polymer on n-Octane/1-Octene Mixtures

During growth on 1-octene, the polymer formed was found to contain both saturated and unsaturated monomers. In order to produce polymers in which the amount of unsaturated monomer is between 0 (after growth on octane) and 55% (after growth on octene; see 6) *P. oleovorans* was cultured on mixtures of these two substrates.

Fermentations, in 1 l stirred tank reactors, were carried out as under 3. In all instances a total amount of 20% organic phase was added. Cell densities and polymer percentages were determined as indicated under 3.

Table 4 shows how the fraction of monomers with double bond varies depending on the composition of the substrate offered, with the monomeric composition being indicated as well. The values indicated were determined on the moment when the polymer content of the cell was maximal.

TABLE 4

Biopolymer production of *Pseudomonas oleovorans* after growth on 1-octene/n-octane mixtures

| n-octane/ 1-octene | fraction of C=C double bond in biopolymer | biopolymer composition | | | |
|---|---|---|---|---|---|
| | | 6:0 | 6:1 | 8:0 | 8:1 |
| 100:0 | 0.0 | 0.11 | 0 | 0.89 | 0 |
| 75:25 | 8.2 | 0.07 | 0.001 | 0.85 | 0.08 |
| 50:50 | 18.4 | 0.06 | 0.01 | 0.75 | 0.18 |
| 25:75 | 30.2 | 0.03 | 0.01 | 0.67 | 0.29 |
| 0:100 | 54.4 | 0.07 | 0.07 | 0.38 | 0.48 |

It can be concluded that, starting from mixtures of paraffins and olefins, the percentage of double bond in the polymer can be varied. Accordingly, the composition of the growth substrate determines (in part) the monomeric composition of the polymer.

8. Formation of Polymer on Other Hydrocarbons

In addition to polymer formation on n-paraffins (see 5) and 1-olefins (see 6) we have also studied whether polymer formation can occur when other, substituted or unsaturated, hydrocarbons are offered as a C source. As *P. oleovorans* is possibly not resistant to all these substrates, they were added in a 1:1 mixture with n-octane.

Fermentations were carried out in 1 l stirred tank reactors as described under 3 using 10-15% organic phase.

Table 5 shows the substrates tested in this manner, and whether, in the case concerned, polymer with different monomers was indeed formed. It was also tested whether 1-octanol, the first intermediate in the decompositon of octane, can be used as a growth and polymer substrate. This was found to be the case when *P. oleovorans* was cultured using 1-octanol as the only carbon and energy source.

It is expected that polymer formation will also occur during growth on further oxidized paraffins (octanal, octanoic acid).

TABLE 5 biopolymer formation by *Pseudomonas oleovorans* during growth on other hydrocarbons

| substrate | biopolymer formation | growth[1] |
|---|---|---|
| n-octane | + | +++ |
| 1-octanol | + | ++ |
| 2-octene | + | + |
| 2-methyl-1-octene | | +++ |
| 1-octyne | − | + |
| 4-octyne | | + |
| 1,3-octadiene | | + |
| 1,4-octadiene | | + |
| 2,2-dimethylheptane | | + |
| 2,2-dimethyloctane | | ++ |
| 2-octanone | − | − |
| n-dibutylether | + | + |

[1]In the column headed by "growth", the codes used have the following meanings:
− no growth
+ moderate growth with a final OD value of between 1 and 5
++ reasonable growth with a final OD value of between 5 and 10
+++ good growth, comparable to growth on octane with a final OD value above 10.

9. Formation of Polymer by Other Strains

All of the experiments described above have been carried out with *Pseudomonas oleovorans* TF4-1L (ATCC 29347). This strain is sometimes designated by GPo-1. In addition to this wild type, a number of related strains were tested for polymer formation after growth on octane or 1-octanol:

GPo-12: GPo-1 without OCT plasmid
PpG-1: *P. putida*, isolated by Chakrabarty; contains no plasmid
PpG-6: PpG-1 with OCT plasmid
PpS-124: PpG-1 with CAM/OCT fusion plasmid.

These strains were tested in 50 ml E*-medium (see 3) in a 250 ml Erlenmeyer flask, using as the carbon and energy source 4% octane or, where the OCT plasmid was absent, 4% 1-octanol.

Table 6 shows what strains form polymer after growth on octane or 1-octanol.

TABLE 6

Production of poly-3-hydroxyoctanoate by GPo-1 related strains.

| strain | plasmid | substrate | amount of polymer (%)[1] | |
|---|---|---|---|---|
| | | | in 50 ml culture | on plate |
| GPo-1 | OCT | octane | 5.9 | |
| GPo-1 | OCT | 1-octanol | 2.9 | |
| GPo-12 | — | 1-octanol | — | 6.1 |
| PpG-1 | — | 1-octanol | 7.7 | 24.8 |
| PpG-6 | OCT | octane | 1.8 | |
| PpS-124 | CAM/OCT | octane | 0.02 | +[2] |

[1]as percent of cellular dry weight, does not apply as an absolute maximum;
[2]clearly detectable.

It can be concluded from the fact that PpG-1, a strain which does not contain a plasmid, stores intracellular poly-3-hydroxyalkanoate that the enzymes involved in the polymer synthesis are coded not on the plasmid but on the chromosome.

The results found prove, or render plausible that polymer formation also occurs when alkanols, aldehydes, carboxylic acids, dialkanols, dialdehydes and dicarboxylic acids are used as a source of carbon.

10. Polymeric Properties of Poly-3-Hydroxyalkanoates

Of the purified poly-3-hydroxyoctanoates-3-hydroxyhexanoate (PHOH) and the purified poly-3-hydroxyoctanoate-3-hydroxyoctenoate-3-hydroxyhexanoate-3-hydroxyhexenoate (PHOHU), the molecular weight (MW), melting temperature ($T_m$) and glass transition temperature ($T_g$) have been determined. The values found are given in Table 7. For comparison, the values of poly-3-hydroxybutyrate (PHB) are also given.

TABLE 7

| polymer | Polymer properties | | |
|---|---|---|---|
| | MW (g/mol) | $T_m$ (°C) | $T_g$ (°C) |
| PHB | $8.0 * 10^5$ | 167 | −4 |
| PHOH | $2.8 * 10^5$ | 56 | −35 |
| PHOHU | $2.8 * 10^5$ | —* | −35 |

—* means that in this case there is no melting point, as the polymeric material is perfectly amorphous.

What we claim:

1. An optically active polyester compound isolated from *Pseudomonas oleovorans* cells cultured in a nutrient medium in the presence of a carbon source and at least one nutrient essential for growth, said carbon source comprising at least one paraffin product containing 6-7 or 9-12 carbon atoms or at least one paraffin oxidation product containing 6-12 carbon atoms, said polyester compound comprising units other than exclusively 3-hydroxyoctanoate units or 3-hydroxyoctanoate and 3-hydroxyhectanoate units having the structural formula:

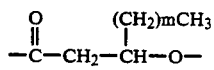

wherein m represents an integer of 2–8.

2. An article of manufacture made from an optically active polyester compound according to claim 1.

3. The article according to claim 2 wherein said article is a suture, a film, a skin graft or a bone graft, 4. An optically active polyester compound isolated from *Pseudomonas oleovorans* cells cultured in a nutrient medium in the presence of a carbon source and at least one nutrient essential for growth, said carbon source comprising at least one compound selected from unbranched 1-olefins containing 7–12 carbon atoms and optionally one or more non-branched paraffins or paraffin oxidation products containing 6–12 carbon atoms, said polyester compound comprising units having the structural formula (1):

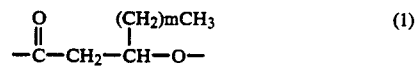

and units having the structural formula (2):

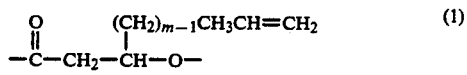

wherein m represents an integer of 2–8.

5. An article of manufacture made from an optically active polyester compound according to claim 4.

6. The article according to claim 5 wherein said article is a suture, a film, a skin graft or a bone graft.

* * * * *